United States Patent [19]

Shell et al.

[11] Patent Number: 4,811,741

[45] Date of Patent: Mar. 14, 1989

[54] VOLUMETRIC DETERMINATION OF A FLUID

[75] Inventors: William E. Shell, Los Angeles; Jackie R. See, Fullerton, both of Calif.

[73] Assignee: See/Shell Biotechnology, Inc., Los Angeles, Calif.

[21] Appl. No.: 899,161

[22] Filed: Aug. 22, 1986

Related U.S. Application Data

[63] Continuation-in-part of Ser. No. 706,151, Feb. 27, 1985, Pat. No. 4,616,658.

[51] Int. Cl.$^4$ ................................................ A61B 5/02
[52] U.S. Cl. .............................. 128/691; 73/861.05; 73/861.07
[58] Field of Search ........... 73/861.05, 861.07, 861.09, 73/149, 861.41; 436/56; 128/691, 630, 666, 691, 692, 694; 424/9

[56] References Cited

U.S. PATENT DOCUMENTS

| | | | |
|---|---|---|---|
| 4,076,419 | 2/1978 | Kleker | 73/149 X |
| 4,417,588 | 11/1983 | Houghton et al. | 128/713 |
| 4,616,658 | 10/1986 | Shell et al. | 128/691 |
| 4,676,252 | 6/1987 | Trautman et al. | 128/692 X |

*Primary Examiner*—Francis Jaworski
*Attorney, Agent, or Firm*—Robert J. Schaap

[57] ABSTRACT

A process for making a volumetric determination of the quantity of a fluid, such as a liquid, by evaluation of a small sample of that fluid. The method comprises labeling microspheres with a non-radioactive substance and introducing the labeled microspheres into a body of fluid for which a determination is to be made. The microspheres are allowed to disperse in the body of fluid. Thereafter, a sample of the fluid which is of know or measurable volume, is selected. The number of microspheres present in the sample is then determined, from which a calculation of the volumetric measurement of the fluid may be made. The process is also adaptable to measuring the flow rate of a moving stream of fluid, since volume is one of the parameters of flow rate, and is also adaptable to determine the percentages of fluid components present in a mixture thereof.

19 Claims, No Drawings

VOLUMETRIC DETERMINATION OF A FLUID

RELATED APPLICATION

This application is a continuation-in-part of our co-pending patent application Ser. No. 706,151 filed Feb. 27, 1985 entitled "Non-Radioactively Labeled Microspheres and Use of Same to Measure Blood Flow" (now U.S. Pat. No. 4,616,658).

BACKGROUND OF THE INVENTION

1. Field Of The Invention

This invention relates in general to certain new and useful improvements in a process for making a volumetric determination of a fluid, and more particularly, to a process for making a volumetric determination of a quantity of fluid by evaluation of a small sample of the fluid using non-radioactively labeled microspheres.

2. Brief Description Of The Prior Art

In many cases, it is desirable to make a volumetric determination of a fluid, such as a liquid, in a container in a fairly rapid and convenient manner. For example, in railroad tank cars, it is relatively easy to determine the volume of a liquid which is present when the tank car is filled to capacity, inasmuch as the volume capacity of the tank car is known. However, when the tank car is not filled to capacity volume, determination of the volume of liquid present is much more difficult. Volume determination can be made by inserting an elongate rod into the liquid to measure the depth of the liquid in the tank car. By knowing the mathematical relationship representing the volume for a given geometry of that tank car, it is possible to determine the amount of liquid present. However, this procedure is not only time consuming, but is not readily adaptable for making a very quick and easy measurement.

In many cases, it is also desirable to measure flow rates of a moving stream of fluid, such as a moving stream of water or to make a volumetric determination of the volume of water flowing past a given point in a given time period in a moving stream of water. It is not difficult to determine fluid velocity when the cross-sectional area of the channel or conduit in which the fluid is moving is known, inasmuch as velocity meters can be employed. Further it is possible to determine the flow rate of a fluid when the channel or conduit cross-section is known or easily determinable. However, in order to determine the volume of a flow, a moderately accurate measure of the cross-sectional area of the stream at the point of determination is required and in many cases this information is not readily available nor easily determinable.

In addition to the foregoing, it is often times desirable to determine the quantity of liquid or other fluid contained in a mixture of liquids or other fluids. For example, if two miscible liquids are mixed, and it is desired to know the percentage of one of the liquids in that mixture, chemical analysis is usually required.

It is therefore desirable to provide a process whereby a sample of a selected liquid from a container can be analyzed to determine the quantity of liquid in that container or to determine the percentages of liquids in a mixture. Further, there is needed a process for making a volumetric determination of the flow rate of a moving stream of liquid by using a small sample thereof. The present invention solves these problems and provides other advantages as well.

OBJECTS OF THE INVENTION

It is therefore, one of the primary objects of the present invention to provide a method of making a volumetric determination of a quantity of a fluid by evaluation of a small sample of that fluid.

It is another object of the present invention to provide a process of the type stated in which the process enables determination of the amount of fluid within a container by evaluation of a small sample of the fluid from that container.

It is a further object of the present invention to provide a process of the type stated for determining the percentages of two or more fluids in a mixture thereof by evaluation of a small sample of that fluid.

It is an additional object of the present invention to provide a process of determining the flow rate and/or the volume of a moving stream of liquid past a given point.

It is another salient object of the present invention to provide a process of the type stated which utilizes labeled microspheres dispersed in a body of fluid and then measuring the number of microspheres present in a known or measurable volume of the fluid.

With the above and other objects in view my invention resides in the novel features of form, arrangment, and combination of steps forming part of the process as presently described and pointed out in the claims.

SUMMARY OF THE DISCLOSURE

The present invention resides in the use of labeled microspheres, and particularly non-radioactively labeled microspheres for making a volumetric determination of a quantity of fluid by evaluating a small sample of that fluid. In a preferred embodiment, the fluid is generally a liquid although the process is applicable with gaseous fluids, as well as fluidized beds of solids which are capable of moving as a stream.

The process involves the labelling of microspheres with a non-radioactive substance, such as a colored dye. Thereafter, the non-radioactively labeled microspheres are introduced into a body of fluid and the microspheres are allowed to disperse in this body of fluid. Generally, and in the case of the measurement of a fluid in a container, a fairly random but yet even distribution of the microspheres should occur.

After the microspheres have been dispersed in the body of the fluid, a sample of the fluid which is of known or measurable volume is then selected. Thereafter, the number of microspheres present in the sample can be determined. By knowing the number of microspheres present in the sample, it is possible to make a relatively simple calculation of the volumetric measurement of the fluid.

In one aspect the process can be used for measuring the volume of a fluid in an enclosure, such as a container. In another embodiment of the invention, the process can be used for determining the percentage of one fluid in a mixture of fluids In still a further aspect of the invention, the process can be used to determine the flow rate of a moving stream of the fluid.

As indicated previously, the non-radioactive substance is a colored dye so that the labeled microspheres are color dyed microspheres. These microspheres are preferably present in a size range of about 7u to about 100u in diameter and more preferably in a range of about 10u to about 50u in diameter.

The method of the present invention involves the labeling of the microspheres with a colored dye. It is also possible to label the microspheres with other substances, such as enzyme markers for a more sophisticated type of determination. However, colored dyes are usually quite effective in enabling a fairly accurate and yet easy determination. "Labelling" is a commonly used term for marking a substance in such manner that the presence of the substance can be later detected.

The microspheres which are used in the present invention may be made of various known compositions as for example, agarose, polystyrene, and styrene, divinylbenzene. The term "microsphere" is used to represent a particle ranging in the size of about 7u to about 100u in diameter. Microspheres within any one size grouping are generally uniform in size. Thus, if a group of microspheres is said to contain particles that are 10u in diameter, all particles would be roughly 10u in diameter with usually no more than a twenty-five (25%) percent variance.

This invention possesses many other advantages and has many other applications which may be made more clearly apparent from a consideration of the forms in which it may be embodied. These forms are described in and form part of the present specification. They will now be described in detail for the purposes of illustrating the general principles of the invention, but it is to be understood that such a detailed description is not to be taken in a limiting sense.

DETAILED DESCRIPTION OF A PREFERRED EMBODIMENT

The present invention utilizes non-radioactively labeled microspheres to make a volumetric determination of a fluid. The microspheres are introduced into the fluid and then allowed to disperse throughout the fluid. For example, in the case of a volumetric determination of a fluid in a container, the microspheres are introduced into the container. If the fluid is in a static condition, slight stirring may be required in order to cause a dispersal of the microspheres throughout the fluid. Generally, there should be a random dispersal but one in which there is a uniform distribution of the microspheres in the fluid.

As indicated previously, the fluid may be a liquid, or it may be a fluidized bed of solid particles. In the case of liquids, the liquid may be either a polar or a non-polar liquid. Thus, the fluid is a substance which does not permanently resist distortion and which is relatively free of shear stress at equilibrium.

The microspheres can be easily dispersed in liquids, such as oil baths in order to determine the quantity of an oil present in a confined area. In like manner, the microspheres can be dispersed in a confined gaseous medium or even in a bed of fluidized solids.

The microspheres are preferably non-radioactively labeled. By using non-radioactively labeled microspheres, the method of the invention poses no health problems to workers and costs are significantly less since there is no need for protection against radioactivity or the need for purchase of radioactive measurement equipment. Further, disposal of the samples with the microspheres is also facilitated since they need not be placed in "low level" radiation dumps.

The term "microsphere" is used to represent particles ranging in size from about 7u to about 100u in diameter. More preferably the microspheres range from about 10u to about 50u. A particular group of "uniformly" sized microspheres may vary in diameter up to about twenty-five (25%) percent. Thus, a group of 10u diameter microspheres might range in size from about 8.5u to about 11.5u in diameter.

The microspheres of the present invention may be composed of any long chain compound susceptible to cross linking to a solid in which amide or carboxyl groups are exposed or are capable of being exposed by suitable treatment. This includes, but is not limited to, latex materials such as polystyrene and styrene divinylbenzene, agarose, polyakylcyanoacrylate, albumin, cross-linked albumin, sucrose, starch, cellulose and dextran. Prefered microspheres are formed of styrene divinylbenzene, which is a latex material, or agarose.

Unlabelled latex microspheres, such as those used in many working examples, are generally stored with a colloidal silica coating, the coated spheres forming a 10% solid suspension in water. Before labeling, the microspheres are cleaned by vacuum filtering and drying.

One method of labeling the microspheres is by dyeing with a water insoluble, colored dye, as described hereinafter. The spheres are placed in chloroform containing the salts of the particular dye desired. After mixing, the microspheres are filtered, washed and stored for use. If the microspheres tend to gather and become bound together in clumps, they are disaggregated by grinding. Successful preparations of uniformly dyed microspheres have been made using the folowwing dyes: Oil Red O, Oil Red EGN, Oil Blue B, Sudan I, Sudan II, Sudan Black B and Fat Brown RR.

The microspheres can be labeled by linking them to an enzyme, as previously described. However, when labeling with an enzyme, a laboratory analysis of the microspheres must then be made. The activity of the microspheres can be measured after dispersal within the fluid. Various forms of enzymes such as animal, plant and bacterial enzymes may be used as the labels. Animal enzymes that may be used included for example, alpha-amylase, beta-galactosidase, alkaine phosphatase, etc. Some of the plant enzymes which may be used are beta-amylase and urease. Bacterial enzymes which may be employed are luciferase and streptokianse.

In order to make a measurement of a volume of e.g. liquid, in a container, a known or a determined number of microspheres are introduced into the unknown volume of liquid in the container. For example, a quantity of sixty-thousand microspheres may be introduced into a container. A sample of 2 liters of the liquid is removed from the container and the number of microspheres is counted. If, for example, the number of microspheres in the sample is determined to be 1000, according to the relationship:

$$\text{VOLUME OF LIQUID (in the container)} = \frac{\text{MICROSPHERES INTRODUCED (into the container)}}{\text{MICROSPHERES IN SAMPLE/SAMPLE VOLUME}}$$

A volume of 120 liters of the fluid would be determined as present in the container since:

$$\text{VOLUME OF LIQUID} = \frac{60{,}000 \text{ microspheres}}{1{,}000 \text{ microspheres}/2 \text{ liters}}$$

It is also possible to determine the percentage of a fluid in a mixture of two or more fluids. For example, if a first type of crude oil designated as Crude A, is mixed with a second type of crude oil, designated as Crude B, it is possible to determine the percentage of Crude A and Crude B present in the final mixture. A first group of colored microspheres of a first color, as for example, red microspheres would be mixed with Crude A oil. A second group of microspheres with a second color, as for example, white colored microspheres, would be mixed with the Crude B oil. When the two crude oils have been mixed, a sample of the mixture of the two crude oils is then obtained. Assuming that an equal number of microspheres were introduced into each of the individual batches of Crude A oil and Crude B oil, a determination of the percentage of each of the crude oils in the mixture can be easily made. If, for example, twenty-five thousand microspheres were introduced in the Crude A oil and twenty-five thousand microspheres were introduced in the Crude B oil and a one gallon sample yielded a total of five hundred microspheres, it would be determined that five hundred gallons of the total mixture is present. Moreover, if two hundred of the microspheres in the sample were of the red color, and three hundred of microspheres were of the white color, then the mixture would contain forty percent of the Crude A oil and sixty percent of the Crude B oil.

In order to measure the flow rate of a fluid, a given quantity of the microspheres are introduced upstream into the moving fluid stream. The amount of time required for at least a certain segment of the microspheres to move past a given point is measured. By selecting a sample of the moving stream of fluid, it is possible to determine the amount of fluid moving past that point in the given time frame.

The flow rate can be determined by the following relationship:

$$\text{FLOW RATE} = \frac{\text{MICROSPHERES TOTAL (added to fluid)}}{\text{MICROSPHERES/CU. FT./MIN. (in sample)}}$$

Thus if 360,000 microspheres are added to a stream of water, and a sample of two cubic feet of the stream of water is collected in a one minute period and which sample contains 8000 microspheres, then the flow rate is 90 cubic feet per minute.

The following describes a specific example of microsphere cleaning and preparation for labeling. The microspheres selected are preferably uniform latex particles 11.9u ±1.9u in diameter. These particles may be obtained from Duke Scientific Product No. 7512A, and come as a 10% colloidal silica solid suspension in water. To prepare the microspheres for labeling, 0.5 ml of the microsphere suspension is vacuum filtered through a Millipore type, 0.45u pore membrane. Whatman No. 542 filter paper will also suffice. The filter support with the microspheres is oven dried at 50-70 degrees C. The dry weight of the microspheres recovered is 44-50 mgs.

As a specific example of labeling microspheres with a colored dye, the microspheres prepared in accordance with the above described example are added to a dye solution consisting of 15 mgs of dye salt in 1 ml of reagent grade chloroform. The melange, in a screw type tube, is gently mixed, end over end, at room temperature for about 18-24 Hours. The melange is transferred to Whatman 1 PS filter paper, which permits the solvent phase to flow through and collects the solids and any contaminating aqueous phase. The dyed microspheres are suspended in-situ in 0.02% (w/v) aqueous Triton ×100 solution for transfer to a wash tube. The dyed microspheres can also be scraped off the paper.

The microspheres, suspended in 5 mls of the above Triton X-100 solution, are gently mixed, end over end, for one hour at room temperature. The microspheres are vacuum filtered as described above and washed three times in-situ with the 0.025% Triton X-100 solution.

If the filtrate at this stage is clear, the preparation is oven-dried at 50-70 degrees C. The microspheres slide off the support, after which they are lightly ground with a glass stirring rod and suspended in 2 mls of distilled water. If the filtrate is not clear, the microspheres must be resuspended in 5 mls. of the Triton X-100 solution, followed by repetition of the mixing and vacuum filtering steps.

Regardless of whether the filtrate is clear, the microspheres are processed as discussed above. The aqueous phase of the suspension is observed for leaching of color from the dyed microspheres. If this occurs, the aqueous phase is removed and replaced.

Using the above procedures, successful preparations of uniformly dyed microspheres have been obtained using the following dyes: Oil Red 0, Oil Red EGN, Oil Blue N, Sudan I, Sudan II, Sudan Black B and Fat Brown RR.

Thus, there has been described a unique and novel process for making volumetric determination of a quantity of fluid by use of measuring labeled microspheres. Thus, the present invention fulfills all of the objects and advantages which have been sought. It should be understood that many changes, modifications, variations and other uses and applications will be apparent to those skilled in the art after considering this specification. Therefore, any and all such changes, modifications, variations and other uses and applications which do not depart from the spirit and scope of the invention are deemed to be covered by the invention.

Having thus described my invention, what I desire to claim and secure by letters patent is:

1. A process for making a determination of the flow rate of a moving stream of a liquid by evaluation of a small sample of the liquid, said process comprising:
   (a) labeling microspheres with a non-radioactive substance to provide non-radioactively labeled microspheres,
   (b) introducing the non-radioactively labeled microspheres into the moving stream of liquid and allowing said microspheres to widely disperse in said moving stream of liquid,
   (c) selecting a sample of the liquid which is of known or measurable volume and which may contain only a small portion of the microspheres which are introduced,
   (d) determining the number of microspheres present in the selected sample of the stream of liquid, and
   (e) calculating the flow rate of of the moving stream of liquid using the determination of the number of microspheres present in the selected sample.

2. The process of claim 1 wherein the non-radioactive substance is a colored dye so that the labeled microspheres are colored dye microspheres.

3. The process of claim 1 wherein said microspheres are sized in the range of about 7u to about 100u in diameter.

4. The process of claim 1 wherein said microspheres are sized in the range of about 10u to about 50u in diameter.

5. A process for making a determination of the flow rate of a stream of fluid by evaluation of a small sample of the fluid, said process comprising:
   (a) introducing non-radioactively labeled microspheres in a moving stream of a fluid and allowing the microspheres to become widely dispersed therein,
   (b) determining the time for a given sample of the fluid stream to pass certain point,
   (c) selecting a sample of the stream of fluid which may contain only a small portion of the microspheres which are dispersed,
   (d) counting the number of microspheres present in the selected sample of fluid, and
   (e) dividing the number of microspheres introduced into the moving stream of the fluid by the number of microspheres present in the sample and using that answer and the time for the given sample to pass a certain point and the number of microspheres introduced into the moving stream to determine the flow rate of the moving stream of fluid.

6. The process of claim 5 wherein the step of selecting comprised removing a selected sample from that stream of fluid.

7. The process of claim 5 wherein the labeled microspheres are colored dye microspheres.

8. The process of claim 5 wherein the labeled microspheres are sized in the range of about 7u to about 100u in diameter.

9. The process of claim 5 wherein said microspheres are sized in the range of about 10u to about 50u in diameter.

10. A process for making a determination of the flow rate of a moving stream of fluid by evaluation of a small sample of the fluid, said process comprising:
    (a) labeing microspheres with a non-radioactive substance to provide non-radioactively labeled microspheres,
    (b) introducing the non-radioactively labeled microspheres into the moving stream of fluid and allowing said microspheres to move with the moving stream of fluid from an upstream position past a selected location,
    (c) selecting a sample of the fluid at the selected location,
    (d) determining the number of microspheres present in the sample, and
    (e) determining the amount of time for the microspheres to move from the upstream position to the selected location, and
    (f) calculating a flow rate of the moving stream of fluid by solving the formula:

$$FR = \frac{MI}{M/SV/TV}$$

where FR=flow rate (of the moving stream of fluid)
MI=microspheres introduced (into the moving stream of fluid at the upstream position)
M=number of microspheres (in the sample)
SV=sample volume (e.g., cubic feet)
Tv=time units (e.g., minutes)

11. The process of claim 11 wherein the fluid is a liquid and the calculating step comprises calculating a flow rate measurement of the liquid.

12. The process of claim 10 wherein the non-radioactive substance is a colored dye so that the labeled microspheres are colored dye microspheres.

13. The process of claim 10 wherein said microspheres are sized in the range of about 7u to about 100u in diameter.

14. The process of claim 10 wherein said microspheres are sized in the range of about 10u to about 50u in diameter.

15. A process for making a determination of a volume of fluid by evaluation of a small sample of the fluid, said process comprising:
    (a) introducing a first group of non-radioactively labeled microspheres into a first fluid,
    (b) introducing a second group of non-radioactively labeled microspheres into a second fluid and which microspheres of the second group are labeled differently than the microspheres of the first group,
    (c) mixing the first and second fluids,
    (d) allowing the non-radioactively labeled microspheres to become widely dispersed in the mixture of the first and second fluids,
    (e) selecting a sample of the mixture of the first and second fluids and which may contain only a small portion of the microspheres which are dispersed,
    (f) counting the number of microspheres present in the mixture of each of the first and second groups, and
    (g) dividing the number of microspheres introduced into the fluids by the number of microspheres present in the sample to determine the volume of the body of fluid.

16. The process of claim 15 wherein the step of selecting comprises removing a sample from the mixture of the fluids.

17. The process of claim 15 wherein the labeled microspheres are colored dye microspheres.

18. The process of claim 15 wherein the labeled microspheres are sized in the range of about 7u to about 100u in diameter.

19. The process of claim 15 wherein said microspheres are sized in the range of about 10u to about 50u in diameter.

* * * * *